(12) United States Patent
Bogie et al.

(10) Patent No.: US 11,478,631 B2
(45) Date of Patent: Oct. 25, 2022

(54) METHODS OF USING AN INTEGRATED SURFACE STIMULATION DEVICE FOR WOUND THERAPY AND INFECTION CONTROL

(71) Applicants: The United States Government, as represented by the Department of Veterans Affairs, Washington, DC (US); Case Western Reserve University, Cleveland, OH (US)

(72) Inventors: Kath M. Bogie, Shaker Heights, OH (US); Steven L. Garverick, Cleveland Heights, OH (US); Christian A. Zorman, Euclid, OH (US); Daniel S. Howe, San Diego, CA (US)

(73) Assignees: THE UNITED STATES GOVERNMENT AS REPRESENTED BY THE DEPARTMENT OF VETERANS AFFAIRS, Washington, DC (US); CASE WESTERN UNIVERSITY, Cleveland, OH (US)

( * ) Notice: Subject to any disclaimer, the term of this patent is extended or adjusted under 35 U.S.C. 154(b) by 1 day.

(21) Appl. No.: 16/229,530

(22) Filed: Dec. 21, 2018

(65) Prior Publication Data

US 2019/0111256 A1    Apr. 18, 2019

Related U.S. Application Data

(60) Division of application No. 14/675,270, filed on Mar. 31, 2015, now Pat. No. 10,201,703, which is a
(Continued)

(51) Int. Cl.
*A61N 1/04*    (2006.01)
*B29C 64/135*    (2017.01)
(Continued)

(52) U.S. Cl.
CPC ......... *A61N 1/0468* (2013.01); *A61N 1/0472* (2013.01); *A61N 1/36031* (2017.08);
(Continued)

(58) Field of Classification Search
CPC .......... A61B 5/6833; A61B 2560/0412; A61B 5/445; A61B 5/0531; A61B 5/01
See application file for complete search history.

(56) References Cited

U.S. PATENT DOCUMENTS 7,970,450 B2 * 6/2011 Kroecker ............. A61B 5/0006
                                                        600/391
2009/0157147 A1 6/2009 Cauller et al.
(Continued)

FOREIGN PATENT DOCUMENTS

| WO | WO-2008/080073 A2 | 7/2008 |
|---|---|---|
| WO | WO-2009/046366 A1 | 4/2009 |
| WO | PCT/US2018/051618 | 9/2018 |

OTHER PUBLICATIONS

POSiFECT(Biofisica) Non patent literature/product, accessed on May 1, 2015. URL: <http://www.wounds-uk.com/journalarticles/bio-electrical-stimulation-therapy-using-posifectrd>.
(Continued)

*Primary Examiner* — Michael J D'Abreu
(74) *Attorney, Agent, or Firm* — Ballard Spahr LLP

(57) ABSTRACT

The present invention provides a thin and flexible device and method of use thereof for wound treatment and infection control. The integrated surface stimulation device may comprise wireless stimulation system in a disposable and/or reusable flexible device for widespread use in multiple therapeutic applications. The invention would be situated on the skin surface of a patient and would be activated so as to reduce the overall occurrence of infections and/or increase wound healing rates. As provided, the device will comprise an integrated power supply and pre-programmable stimula-
(Continued)

tor/control system on a flexible polymeric substrate layer with areas of stimulating electrodes, applied using techniques such as those found in additive manufacturing processes. The device is especially valuable in treating biofilm-based infections.

20 Claims, 5 Drawing Sheets

Related U.S. Application Data continuation of application No. 14/363,277, filed as application No. PCT/US2013/022139 on Jan. 18, 2013, now Pat. No. 9,320,907.

(60) Provisional application No. 61/594,105, filed on Feb. 2, 2012.

(51) Int. Cl.
| | | |
|---|---|---|
| *A61N 1/36* | (2006.01) | |
| *B29K 79/00* | (2006.01) | |
| *B29K 105/16* | (2006.01) | |
| *B29K 505/14* | (2006.01) | |
| *B29L 31/00* | (2006.01) | |
| *B33Y 10/00* | (2015.01) | |
| *B33Y 50/02* | (2015.01) | |
| *B33Y 80/00* | (2015.01) | |

(52) U.S. Cl.
CPC ........ *B29C 64/135* (2017.08); *B29K 2079/08* (2013.01); *B29K 2105/16* (2013.01); *B29K 2505/14* (2013.01); *B29K 2995/0005* (2013.01); *B29L 2031/753* (2013.01); *B33Y 10/00* (2014.12); *B33Y 50/02* (2014.12); *B33Y 80/00* (2014.12)

(56) References Cited

U.S. PATENT DOCUMENTS

| | | |
|---|---|---|
| 2009/0242854 A1 | 10/2009 | Li et al. |
| 2010/0174343 A1* | 7/2010 | Andino ................. A61N 1/205 607/50 |
| 2010/0241057 A1* | 9/2010 | Pak ........................ A61N 1/044 604/20 |
| 2012/0190956 A1* | 7/2012 | Connolly ............ A61F 13/0253 600/372 |
| 2014/0163641 A1 | 6/2014 | Yao et al. |
| 2014/0206947 A1* | 7/2014 | Isserow .............. A61N 1/36021 600/301 |
| 2015/0343205 A1 | 12/2015 | Howard et al. |
| 2016/0074664 A1 | 3/2016 | De Ridder |
| 2016/0101282 A1* | 4/2016 | Bergelin ............... A61N 1/0496 600/547 |
| 2016/0220135 A1 | 8/2016 | Negi et al. |
| 2016/0339239 A1 | 11/2016 | Yoo et al. |
| 2017/0043164 A1 | 2/2017 | Biele et al. |

OTHER PUBLICATIONS

Procellera Wound Dressing Non patent literature/product, accessed on May 1, 2015. URL: <http://procellera.com/procellera/technology>.

Various Devices, Including GV350 model (Biomedical Life Systems) Non patent literature/product, accessed on May 1, 2015.

Wound EL (Mölnlycke Health Care) Non patent literature/product, accessed on May 1, 2015. URL: <http://www.molnlycke.com/advanced-wound-care-systems/electrical-stimulation/#confirm>.

International Search Report and Written Opinion dated Jan. 28, 2019 by the International Searching Authority for Patent Application No. PCT/US2018/051618, which was filed on Sep. 19, 2018 and published as WO 2019/060332 dated Mar. 28, 2019 (Inventor—Zoman et al.; Applicant—The United States Governement as Represented by the United States Department of Veterans Affairs; (15 pages).

U.S. Appl. No. 61/594,105, filed Feb. 2, 2012, Kath M. Bogie (U.S. Government, Represented by the Dept. of V.A.).

U.S. Appl. No. 14/363,277 (U.S. Pat. No. 9,320,907), filed Jun. 5, 2014 (Apr. 26, 2016), Kath M. Bogie (U.S. Government, Represented by the Dept. of V.A.).

U.S. Appl. No. 14/675,270 (U.S. Pat. No. 10,201,703), filed Mar. 31, 2015 (Feb. 12, 2019), Kath M. Bogie (U.S. Government, Represented by the Dept. of V.A.).

U.S. Appl. No. 62/560,551, filed Sep. 19, 2017, Kath M. Bogie (U.S. Government, Represented by the Dept. of V.A.).

\* cited by examiner

Fabrication sequence with a polyimide substrate

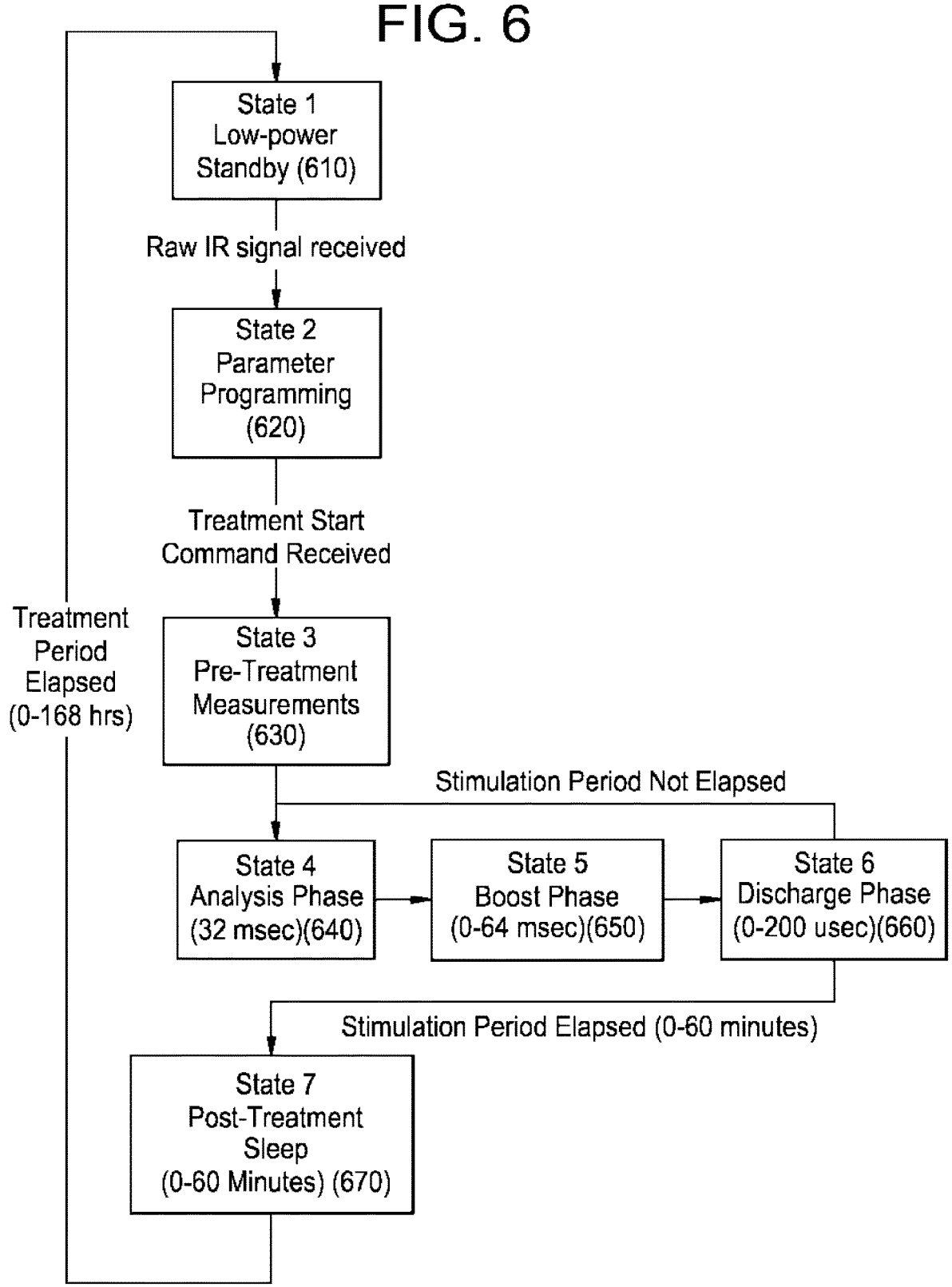

METHODS OF USING AN INTEGRATED SURFACE STIMULATION DEVICE FOR WOUND THERAPY AND INFECTION CONTROL

CROSS-REFERENCE TO RELATED APPLICATIONS

This application is a division of U.S. patent application Ser. No. 14/675,270, filed on Mar. 31, 2015, which is a continuation in part of U.S. patent application Ser. No. 14/363,277, filed on Jun. 5, 2014, now U.S. Pat. No. 9,320,907, which is a Section 371 national phase of International Patent Application No. PCT/US2013/022139, filed on Jan. 18, 2013, which claims priority to and the benefit of the filing date of U.S. provisional patent application No. 61/594,105, filed on Feb. 2, 2012. The contents of each of the above-identified applications is hereby incorporated by reference in its entirety.

FIELD OF THE INVENTION

The present invention relates to medical devices that utilize electrical stimulation for surface-stimulated treatment of pain and wounds in the human body. The present invention is a patch, i.e. a thin, partially flexible covering, which incorporates a stimulation controller, wireless communication device, miniaturized or wireless power, and a substrate with customizable treatment electrodes.

Open wounds can be difficult to treat. In particular, chronic wounds, such as ischemic wounds and pressure ulcers, are a major clinical challenge in the long-term care of people with physical impairment and/or disability. Even in mild cases, special care is required. Scientific studies show that electrical stimulation quickens wound healing, reduces scar formation, and can reduce discomfort therefrom. For example, galvanic treatment has been known for many years as a means to deliver drugs and cosmetic active agents into the skin for therapeutic purposes. Such approaches are based on mechanisms such as iontophoresis and electro-osmosis. A review of the literature reveals that galvanic treatment is also valuable in the treatment of wounds and scars, via several modes of action including accelerated cell regeneration; tissue repair; accelerated cutaneous barrier recovery (even with very low current); improved blood circulation; improved respiration; and scar reduction. Examples of such devices may be found in US Pat. Pub. No. 2010/0228180, titled "Power Source Electrode Treatment Device". PCT Pat. Pub. No. WO 2006/072834, titled "Stable Electrode and Uses Thereof, European Pat. Pub. No. EP 1448263, titled "Device for Controlled Delivery of Active Substance into the Skin, U.S. Pat. No. 7,922,676, titled "Disposable Electric Bandage", and U.S. Pat. Pub. No. 2010/0030129, titled "Dermal Patch", each of which is hereby incorporated by reference in their entireties. In yet another example, clinical studies have used direct current (DC) electrical stimulation for electrotherapy. In summary, clinical studies have used different stimulation approaches and also surgical implantation, but to date no optimum electrotherapy protocol has been identified, especially for problematic wounds such as pressure ulcers.

Current approaches to electrical treatment have not been widely used in wound and/or pain therapy because these treatments comprise stationary, costly stimulation devices which are not convenient for home use. Furthermore, existing treatment protocols are simplistic administrations of electrical current that do not account for the need for varied modalities of treatments for specific wound types and pain associated therewith. More specifically, known approaches for wound treatment and ameliorating pain tend to require a high degree of technological expertise and training both for introduction and regular use, and often, surgical expertise is essential for implantation of these systems. Even where technologies are employed that negate the need for surgical implantation, existing devices are nevertheless intrusive and tend to disrupt other therapies and the activities of daily living in part because they utilize external wires and cables for use and powering of surface electrical stimulation devices. In addition to limiting patient mobility through the need to connect and disconnect wires whenever the patient moves, these very same wires are also a common source of device failure. Moreover, there has not been any notion either in literature or in common practice of combining wound care and pain treatment in wound therapy, or of providing customizable solutions to the exact treatment of the various forms of these maladies.

To this end, there is a recognized need for a simple, reliable, low-cost integrated surface stimulation device (ISSD) that can be used in a variety of mobile care settings, from the intensive care unit to the patient's home. It would be highly advantageous for this ISSD to have such an ISSD that employs electrical stimulation for wound and/or pain treatment, embodied on a thin and flexible substrate that includes a self-contained power source and controller. Preferably, such a system and device should be disposable and customizable for particular types of wounds and pain associated therewith, including the treatment protocol itself.

SUMMARY OF THE INVENTION

The present invention relates to a novel approach to improving the management of pain and wound healing through the use of an integrated surface stimulation device (ISSD). The ISSD for pain management, according to the present invention, is a wearable, flexible adhesive electrical stimulation patch that is wireless, with the totality of the component electronics and power source being wholly encapsulated thereon in a thin, flat instantiation. In providing the above, the invention utilizes advanced materials and fabrication techniques, and is designed so as to have a simple, user-friendly communication interface. More specifically, one embodiment of the invention contains all the components of a single-channel, current-controlled stimulation system within a lightweight, flexible, independently-powered portable device utilizing a custom, miniaturized (approximately 9 mm$^2$) Application-Specific Integrated Circuit (ASIC), also known as a custom IC. The ISSD uses advanced materials and cutting-edge fabrication techniques to provide sustained or intermittent application of Electrical Stimulation (ES) combined with maintenance of a stable wound healing environment. An optional software package with a graphical user interface (GUI) may also be provided for use on a partner device connected to the invented device, to be employed by a medical professional.

The ISSD comprises a complete wireless stimulation system in a disposable and/or reusable flexible device for widespread use in multiple therapeutic applications. The invented device would be situated on the skin surface of a patient and would be activated so as to reduce the overall occurrence of pain and/or increase wound healing rates. As manufactured, the device will comprise an integrated power supply and pre-programmable stimulator/control system mounted on the upper face of a flexible polymeric 'backbone' or substrate layer. The lower face of the substrate layer will comprise areas of stimulating electrodes, applied using thin film deposition techniques such as sputtering, evaporation, electroplating, and spray coating. The device can then be applied to the user with a medical grade pressure sensitive adhesive coating provided on the lower face of the substrate layer.

When provided as such, the invented system has features which also make it advantageous for patients when compared with conventional systems, in that it offers the advantage of electrical stimulation of the nerves that allows for better pain management, but does so in a miniaturized, wholly self contained reusable wireless adhesive patch-like device that can be worn on a patient's skin. To this end, the present invention overcomes the aforementioned and other disadvantages inherent in the prior art.

BRIEF DESCRIPTION OF THE DRAWINGS

With reference now to the drawings in detail, it is stressed that the particulars shown, are by way of example and for the purposes of illustrative discussion of embodiments of the present invention, and are presented for providing what is believed to be the most useful and readily understood description of the principles and conceptual aspects of the invention. In this regard, no attempt is made to show structural details in more detail than is necessary for a fundamental understanding of the invention, the description taken with the drawings making apparent to those skilled in the art how the several forms of the invention may be embodied in practice. Accordingly:

FIG. 6 is an operational flow diagram illustrating an exemplary treatment protocol utilized with one embodiment of the invention.

DETAILED DESCRIPTION OF THE PREFERRED EMBODIMENTS

Figure 1:
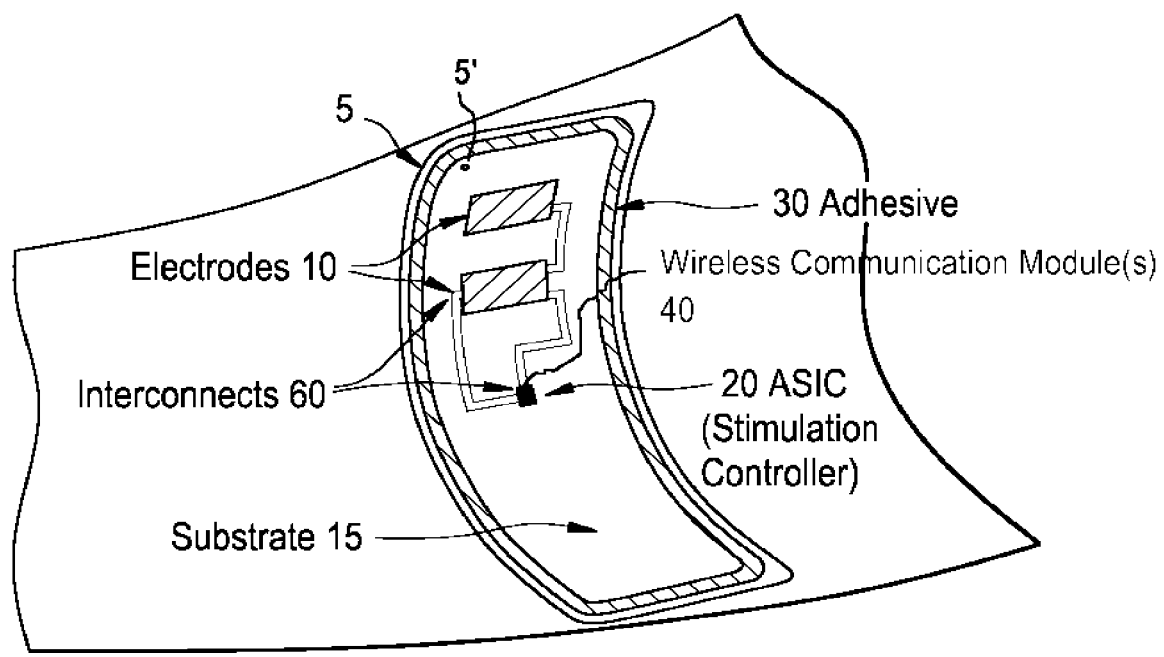
FIG. 1 is a photograph showing the physical appearance of an incomplete prototype of a wound treatment device as applied to a user, according to one embodiment of the invention.

Before explaining at least one embodiment of the invention in detail, it is to be understood that the invention is not limited in this application to the details of construction and the arrangement of the components set forth in the following description or illustrated in the drawings. The invention is applicable to other embodiments of being practiced or carried out in various ways. Also, it is to be understood that the phraseology and terminology employed herein is for the purpose of description and should not be regarded as limiting.

At its broadest level, the present invention relates to a medical device for treatment of wounds or pain comprising at least one electrically powered patch comprising ISSD circuitry that includes interconnecting wires on a substrate layer; at least one stimulation controller, the stimulation controller being configured so as to provide variable stimulation patterns; at least one configuration of electrodes attached to the substrate layer and in electrical connectivity with the at least one stimulation controller; at least one bi-directional wireless communication link, the bi-directional wireless communication link or module comprising at least one RF or infrared based interface; at least one power source electrically coupled to at least one configuration of electrodes and at least one stimulation controller. The ISSD must also include means for encapsulating the circuitry; and an adhesive means for attaching the substrate layer to a treatment surface. The device is fabricated from thin and flexible materials to enable at least those surfaces that contact a patient skin to conform to the contour of the patient, and may be processed with thick or thin film deposition techniques for application of the electrodes and other circuitry components, and may also provide for the power source to also feature a thin and flexible profile.

The principles and operation of powered treatment devices according to the present invention may be better understood with reference to the figures. The figures show exemplary embodiments of the present invention and are not limiting.

Figure 2:
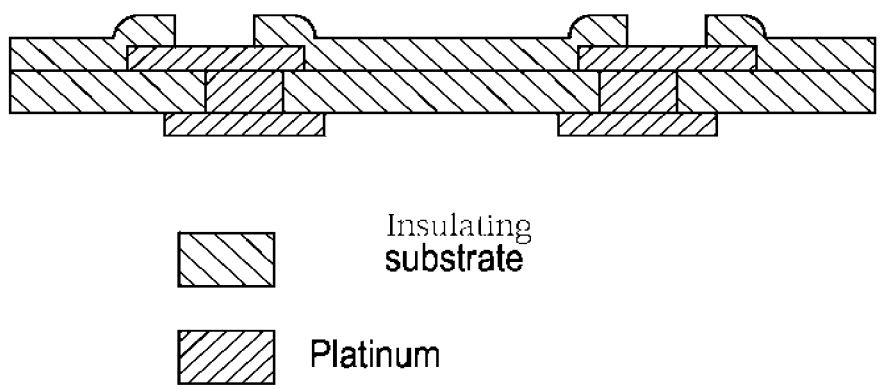
FIG. 2 is a schematic representation of an exemplary cross section of ISSD electrode-supporting substrate in accordance with one embodiment of the invention.
Figure 3:
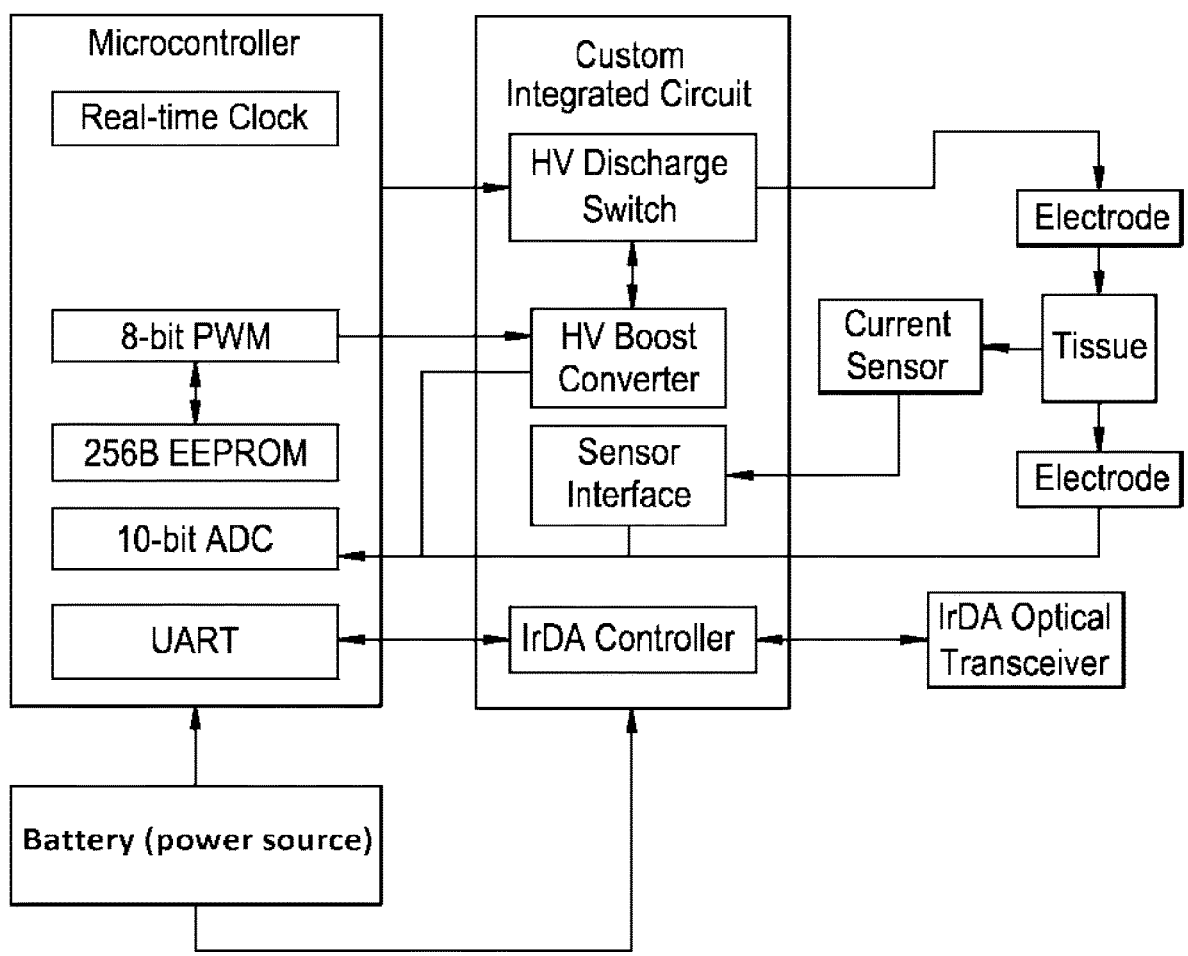
FIG. 3 is an illustrative block diagram of flexible ISSD circuitry 60 and related peripheral electronic components of the device according to one embodiment of the invention.
Figure 4:
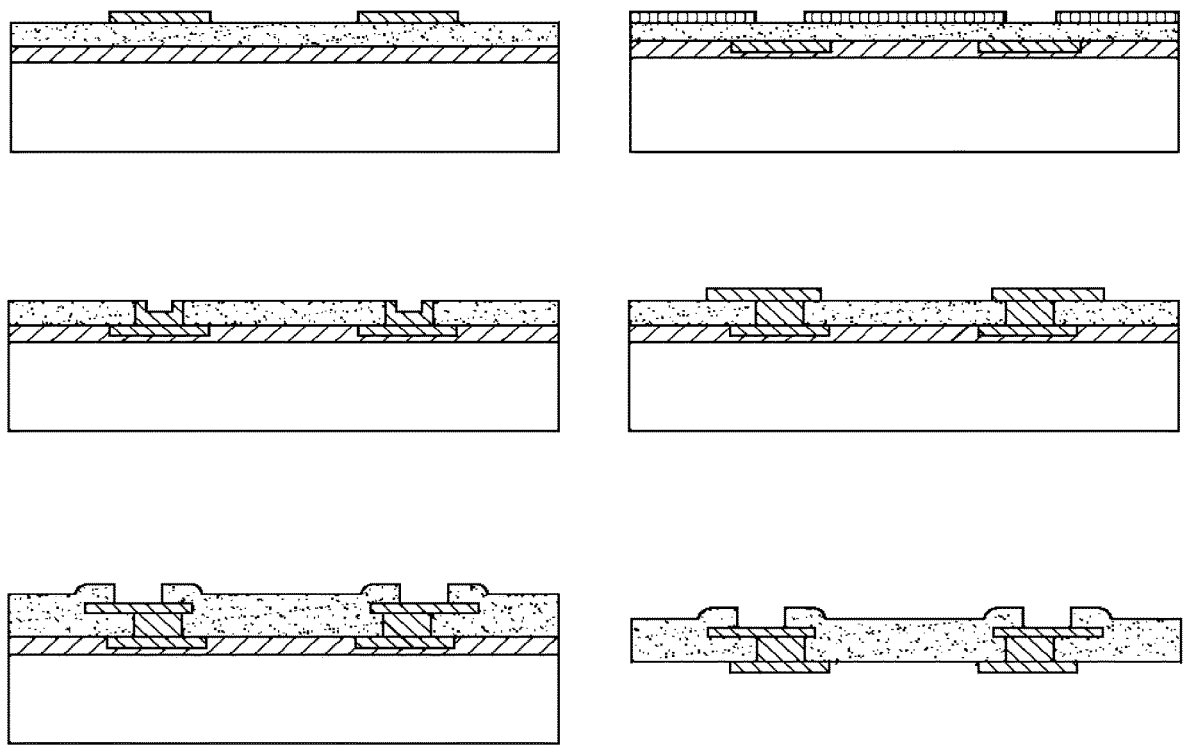
FIG. 4 is schematic cross-sectional views illustrating an exemplary fabrication sequence with polyimide substrate used in the device in accordance with one embodiment of the invention.
Figure 5:
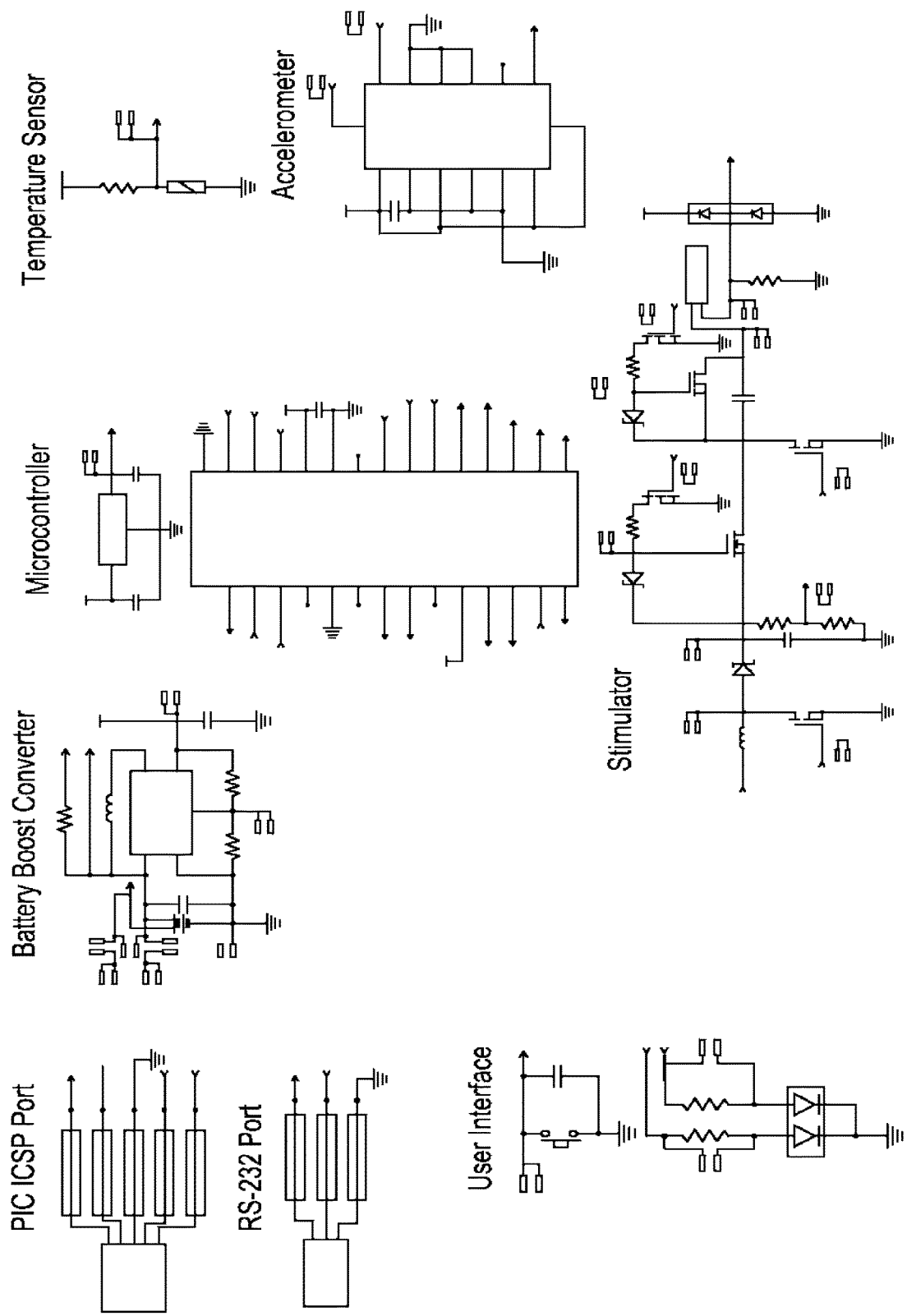
FIG. 5 is an electrical schematic diagram of one embodiment of the device according to the invention.

FIG. 1 shows one embodiment or a powered treatment device 5, including only the stimulation electrodes and controller components of the ISSD circuitry 60, where the latter has been fully implemented as an ASIC in order to reduce size and improve flexibility of the device. FIG. 2 shows the schematic cross-section of the supporting substrate, which is optionally made of flexible materials. FIGS. 3 and 5 show two additional embodiments of stimulation controller 20, one (FIG. 3) which employs an ASIC (custom IC) to implement only the high-voltage, sensing, and wireless communication modules 40 of stimulation controller 20, and another (FIG. 5) in which off-the-shelf (OTS) components have been used to implement these functions. In both embodiments, stimulation controller 20 must be interconnected with the electrodes 10 through interconnecting wires 17 (not specifically depicted) and electrically connected with power source or supply 50, all of which are carried by a disposable substrate layer 15. Power supply 50 and stimulation controller 20 components can be bonded to the upper face or side of substrate 15. Flexible stimulating electrode 10 regions can be microfabricated onto the lower face or side, which will be secondarily coated with a medical grade pressure sensitive adhesive for attachment to the user. Because one key design concept underlying inventive device 5 is forward compatible upgrade ability, it is provided with a flexible or adaptable architecture that allows for the potential for functional expansion such as multi-channel stimulation and biofeedback sensor capability, which is provided as an alternate embodiment of the present invention. The device comprises an integrated power supply and pre-programmable stimulation controller 20 system mounted on the upper face of a flexible polymeric 'backbone' or substrate layer 15. The lower face of substrate layer 15 comprises areas of stimulating electrodes 10, applied using sputter coating techniques as described hereafter and as illustratively shown in FIG. 4. The device can be applied to the user with a medical grade pressure sensitive adhesive coating 30. In most cases, it may be helpful to have device 5 sterilized upon reuse or where not initially sterilized prior to placement over an open wound area of a patient. Many approaches may be used for this, and one illustrative sterilization could involve using an ethylene oxide, which is a low-temperature method that would allow device 5 to be fully sterilized, but would not damage the on-board electronics.

The controller circuitry or stimulation controller 20 provides functions such as timing, intermittent operation, and power monitoring, and combines with passive components, such as resistors, capacitors, an inductor and connective wiring (interconnecting wires 17, not specifically depicted), to produce stimulating waveforms. The duty factor of the high-voltage discharge pulses produced using stimulation controller 20 will be proportionally related to the average output power. The aforementioned passive elements are usually separate components, and may, in one embodiment, be mounted to a rigid circuit board (not depicted) and can be connected by printed wiring (also not depicted). However, a traditional rigid circuit board may not always meet design requirements (such as specific types of required flexibility) that may be required in some embodiments for stimulation controller 20. In either case, all electronic components herein must be minimized in quantity and size to maximize flexibility, as will be further discussed below.

Depending on the desired effect and system requirements, one may employ one of three possible illustrative embodiments, wherein the stimulation controller 20 comprises either: (i) two ICs (an IC microcontroller coupled with an ASIC stimulator); or (ii) a single IC (e.g., an IC microcontroller coupled with an OTS discrete stimulator); or (iii) a full-function IC, i.e. an ASIC that includes both stimulator and microcontroller functions, each of which is preferably miniaturized.

The ASIC embodiment may be either partially or completely based on an ASIC that may include all circuit functions required for actuation and sensing of the ISSD, as well as communication to the external computing device, such as a laptop computer, smart phone or the like, as contrasted with the discrete stimulator mentioned above which provides for these components separately. In either case, a high-voltage transistor may be required as part of a boost converter that provides the approximately 100-V level required for electrical stimulation in some circumstances. In one embodiment, all boost converter circuitry, excluding the aforementioned high-voltage inductor, diode, and storage capacitor components, could potentially be integrated onto the ASIC. Analog preamplifiers and analog-to-digital converter for sensing of electrode current and other biological signals of interest can also be fully integrated. Wireless communication circuits that comprise the wireless communications module 40 (discussed hereafter) can also be fully integrated, except for the infra-red (IR) photo diodes based embodiment required by the illustrative IrDA channel when used in a rigid circuit board-based embodiment. Because IR-based connectivity approaches require line-of-sight to a given partner device, in one illustrative embodiment, wireless communications can employ alternative wireless communication approaches such as the Bluetooth® Low Energy (version 4.0) standard, or other RF approaches for wireless communications module 40. The inventive flexible ISSD circuitry 60 may then comprise at least: (i) a stimulation controller 20 mounted on a circuit board which is in turn mounted on substrate layer 15, wherein the stimulation controller 20 has different embodiments, either two ICs (an IC microcontroller coupled with an ASIC stimulator); or a single IC (e.g., an IC microcontroller coupled with an OTS discrete stimulator); or a full-function ASIC that provides both microcontroller and stimulator functions, as discussed herein); (ii) a bi-directional wireless communications module 40 which includes connectivity to an IR interface (photodiode pair) or an RF interface required for wireless communication; (iii) a high-voltage boost converter circuit in electrical connectivity with stimulation controller 20, said high-voltage boost converter circuit comprising an appropriate high-voltage inductor/diode/storage capacitor as required by stimulation controller 20, said high-voltage boost converter circuit being charged to the aforementioned high-voltage level; (iv) power source 50 connected to the circuit board upon which stimulation board 20 is mounted; (v) stimulating electrodes 10 connected an interconnection means to the circuit board upon which stimulation board 20 is mounted; and (vi) the interconnecting means, wherein the interconnection means is provided for electrically connecting at least stimulating electrodes 10 with stimulation controller 20, the interconnection means illustratively including at least one or more components chosen from the group comprising: interconnecting wires 17 (not specifically depicted); thin film deposited structures; or thin film platinum interconnect structures in combination with a bonding, wherein the bonding is chosen from the group comprising wire bonding or flip chip bonding. In contrast to the full-function ASIC embodiment, the two-IC embodiment offers a separate high-voltage stimulator ASIC and microcontroller in order to permit straight-forward firmware upgrades and to minimize the cost of the ISSD, given that inexpensive OTS microcontrollers can be employed. This embodiment provides for the function of the stimulator to be preserved in the case where the microcontroller requires upgrading. The stimulator may be implemented using any preferred technology independent of the microcontroller and furthermore, may include sensory circuits such as for monitoring movement or other vital statistics in a user. In any case, the above ISSD circuitry can be encapsulated via an encapsulation means that protects the same from moisture and the like, all of which, when mounted on substrate layer 15, can be adhered to the skin of a user through the adhesive means described herein.

Regardless of the particular embodiment of stimulation controller 20, ISSD circuitry 60 may employ an aforementioned high-voltage boost converter circuit with a step-up loop that includes the aforementioned high-voltage transistor, and a storage capacitor that is rated for an illustrative maximum 100V, at an illustrative 100-nF capacity in order to maximize the voltage aspects of the overall system, and for increasing the (interchangeable) battery life of power source 50. In both the two-IC embodiment and the full-function ASIC embodiment, the step-up capacitor may be provisioned to be physically separate, off chip, but in electrical connectivity therewith. In the particular case of the two-IC embodiment, both ICs can be obtained in die form and can be 1) flip-chip bonded directly to metal traces on the flexible substrate, then scaled with protective coating, or 2) wire bonded to the lead frame of a standard surface-mount IC package that would then be hermetically scaled. The former is potentially smaller and more flexible, while the latter is simpler to manufacture and potentially more robust. Where an embodiment is desired that includes customized rather than OTS ICs, a custom IC (ASIC) could be fabricated using an illustrative 0.7-micron high-voltage CMOS foundry process provided by ON Semiconductor (available from ON Semiconductor of Phoenix, Ariz.), via the MOSIS service of Marina del Rey, Calif. Thereafter, it is noted that in the present invention, variable stimulation patterns are provided to accommodate different types of wounds and the changing treatment thereof over time. To this end, software can be pre-programmed on the microcontroller of a two-IC embodiment, or on the ASIC of a full-function ASIC embodiment. The various parameters that may be considered when providing such software within device 5 might, in one embodiment, be effected through usage of the below considerations set forth in Table 1, below.

TABLE 1

Specifications for conformable flexible modular surface stimulation (MSS) device

| Variable | Relevance | Criteria |
|---|---|---|
| Safety | Prolonged contact with skin requires neither the materials employed nor the stimulation delivered will cause tissue damage | Substrate materials must be biocompatible & stimulation may be charge-balanced. |
| Reliability | In order to be effective, ES must be delivered as programmed. | Stimulation is ideally delivered consistently over an illustrative 7 day lifetime of the device. |
| Sterilization | Devices in contact with open wounds must be initially sterile to minimize infection. | May use illustrative ethylene oxide sterilization to achieve sterility while maintaining electrical functionality. |
| System configuration | | |
| Flexible | Chronic wounds occur on many parts of the body. | Conform to an are equal in radius to a circumference of any rounded body parts. |
| Size | Device must be suitable for clinical use in a variety of wound locations. | Overall footprint will vary to fit target wound. |
| Electrode layout | Stimulating electrodes deliver therapeutic ES to the wound. | Electrodes to be located at the wound margins and can be patterned based on wound size and shape. |
| Low-profile & lightweight | Not interfere with overlying bedclothes or cause high pressure if accidentally lain on. | Maximum height less than 3 mm in one illustrative embodiment. Maximum weight less than 15 g in one illustrative embodiment. |
| System function | | |
| Wound occlusion | A moist microenvironment provides optimal wound healing | Maintenance of adherence to skin for up to 7 days with full wound occlusion. |
| User-friendly interface | Clinical acceptance requires case-of-use. | Includes a customizable design for an intuitive GU1 for selection and control of stimulation patterns. |
| Programmable | Optimal stimulation variables for ES therapy remain to be defined. Stimulation can be applied intermittently or continuous, for duty cycles From 5 min/day to 24 h/day. | Stimulation pulse variables may be based on data from prior clinical studies, illustratively described as: Range Increment; Pulse width 0-200 μs 5 μs; Amplitude 0-20 mA 0.5 mA; Frequency 0-20 Hz 1 Hz |
| Power supply | Independent power supply, capable of 7 days use is required for un-tethered system. | Battery-powered, capable of up to 7 days continuous use. Battery will last longer with intermittent use. |

As mentioned above, the central core of present device 5 is comprised or a flexible polymeric biomaterial substrate (substrate layer 15) on which the flexible power supply 50 and rigid stimulation controller 20 will be attached along with the thin metallic electrodes and interconnects that are fabricated thereon. In certain illustrative embodiments, three different polymeric materials may be used to construct the flexible structures of the substrate layer 15, specifically materials such as polyimides, liquid crystal polymers, and thermoplastic polymers. In one particular embodiment, a combination of thick polyimide foils and thin film resins may be used for producing substrate layer 15 in order to meet the requirements for the device to be durable for longer periods in different environments, such as those encountered where use is needed for say, one week of continuous use in moist environments. One illustrative example of production of this variant of substrate layer 15 within the overall context of the present invention may be seen in FIG. 4, which details an exemplary process sequence for fabricating a flexible polyimide ISSD substrate. Substrate layer 15 may optionally be manufactured from any polymer material that is suitable for flexible electronics and biomedical uses according to a process that utilizes patterning that creates via structures thereon between the aforementioned circuit components through use of a micromachining step, or any suitable material which can accommodate the powered treatment device components. Suitable materials include, but are not limited to woven material, non-woven material, polymers, or a combination thereof, and, in the case of woven materials might alternatively include the usage of smart fabrics which employ conductive traces on or within the fabric whether purely woven, knitted, sewn, couched, or whether provided as e-broidery and/or printed structures. Nevertheless, in one illustrative embodiment, substrate layer 15 may alternatively be made from liquid crystal polymers, polyimides, vinyl materials or polyester. Optionally, substrate layer 15 can be made up of a plurality of materials, which can be stacked or connected in a co-planar way by any suitable attachment means. In some embodiments, base layer substrate 15 is made up of one continuous piece of material. Substrate layer 15 may readily facilitate attachment of the overall device 5 to a desired body area. Attachment mechanisms may include but are not limited to medical grade adhesives, adhesive strips, suction cups and/or any combinations thereof. It has also been found that lower cost medical grade pressure sensitive adhesives such as Dermabond® (2-octyl cyanoacrylate, marketed under the aforementioned trademark by Johnson & Johnson of New Brunswick, N.J.) can be used, in one embodiment, to attach substrate layer 15 to intact skin. On removal, this type of medical grade pressure sensitive adhesive preferentially adheres to the substrate material, thus causing no skin damage, and can remain strongly adherent after many hours or days.

In one embodiment, the present invention provides flexible ISSD circuitry 60 to be situated on substrate layer 15 that is processed from an illustrative polyimide material that utilizes patterning processes in order to create via structures between the circuit components of flexible ISSD circuitry 60. One exemplary approach utilizes micromachining step, such as a KOH-based wet chemical etching step, in order to create the via structures depicted in FIGS. 2 and 4. Such an etchant is effective in removing polyimide, and the use of etchant-resistant materials such as platinum for electrodes 10 and the metallic etch mask can offer good resistance to the etchant. Alternatively, plasma etching, laser micromachining or other material removal techniques can be utilized to realize the same structures, but in either case, successful fabrication of the flexible ISSD circuitry 60 is critically dependent on the fabrication of effective interconnect structures that fill the microfabricated vias. Simultaneous electroplating on both the sidewalls and the bottom surface of the vias enables complete filling within an illustrative current thickness range of say, 10 microns. Alternative electroplating options may be afforded under ultrasonic conditions or with the use of 'filler' materials. Following fabrication of substrate layer 15 and interconnects thereon, the discrete components thereof can be mounted at designated locations on the (illustrative polyimide) substrate layer 15 using a conventional electronics packaging adhesive. Electrical connections that may comprise a part of an interconnection means or in one embodiment, interconnecting wires 17, between the discrete components and the thin film platinum interconnect structures may, in one illustrative embodiment, be made by wire bonding. Flip chip bonding can also be used to make secure electrical connections. The electrical connections can be mechanically secured, electrically isolated and environmentally protected by a third polyimide film of roughly the same thickness as the discrete components (0.5 mm) so as to ensure complete coverage of the wire bonds. It can be locally applied so as to not interfere with the global flexibility of the substrate. After localized polyimide encapsulation, the polyimide substrates can be removed from their silicon wafer pairs by a mild acetone soak or other appropriate methodology as known in the art.

In an additional embodiment, the present invention provides a method of production of device 5 and details of which, in terms of the illustrative materials and fabrication, are discussed henceforth. The central core of the device 5 is a flexible electrode-supporting substrate 15 comprised of a Liquid Crystalline Polymer circuit material (LCP) sheet with an 18 μm copper cladding layer on one of its surfaces, the fabrication sequences of which are illustratively described in one embodiment as seen in FIG. 4. In one embodiment, the electrode structures 10 are fabricated on the non-copper clad user-applied side of the LCP substrate 15 by photolithographic patterning, platinum thin film sputtering, and lift-off patterning. Electrodes 10 can be made of any suitable material, such as zinc, copper, manganese dioxide, iron, magnesium, silicon, sodium, silver, silver/silver chloride, carbon, graphite, platinum, nickel, gold, lithium or a combination thereof. Optionally, electrodes 10 can be made by any suitable technique. In some embodiments, electrode is made by a suitable printing technique. Electrodes 12 can be disposed in any suitable way on substrate 15 in spaced relation to power source 50 and electrically connected to power source 50 in any suitable way, or as described herein. Vias for vertical electrical interconnects between the two sides are then formed through the LCP by laser micromachining or plasma etching from the copper-clad component side to the back of the platinum electrodes. Platinum is sputter deposited on the sidewalls of the vias prior to electroplating to form a vertical interconnect between the bio side electrodes and the stimulation circuitry on the component side, as depicted in FIG. 2 and FIG. 4. Lateral interconnect structures are then fabricated by lithographic patterning and copper etching. The upper surface of the substrate 15 can be composed of a flexible barrier material (optionally part of the aforementioned encapsulation means) that provides a safe interface with the patient's environment, yet protects the electrical components from direct exposure to moisture, especially for the sensitive and delicate microprocessor chips and electrical interconnects. This packaging or encapsulation means must not impede the flexibility of the substrate, be impervious to impurity diffusion, be mechanically durable and be electrically insulating. Parylene is one embodiment for this application since it meets the design requirements and has been found to be a suitable candidate coating material for implanted medical devices. The lower side of substrate 15, which is intended to be applied to the skin of a patient, is secondarily coated with a medical grade pressure sensitive adhesive for attachment to the user, as part of the aforementioned adhesive means. The metalized surfaces on the component side are passivated by the application of a vapor deposited Parylene film and/or spin-castable polymer. Windows into the passivation layer can be formed by laser micromachining or plasma etching to facilitate electrical connection with discrete components, and can provide patterning in varying layouts as may be required for customized electrode patterns in specific applications involving particular (size/type) wound remediation and the like. In order to meet the need for customization, the above offers an aspect of provision for modularity wherein the electronic components of ISSD circuitry 60 can be mounted on a second LCP sheet that serves as the substrate for the reusable electronic components. Interconnect structures are fabricated on this LCP sheet using the methods described above. Therewith, further connections between the electronic components and the interconnect structures, including the interconnection means, can also be made by wire bonding or flip chip bonding. The reusable component substrate can then mounted on the electrode-supporting substrate using a conventional packaging adhesive. The reusable component substrate is mechanically secured, electrically isolated and environmentally protected by an encapsulating means of polymer film of roughly the same thickness as the discrete components (0.5 mm) so as to ensure complete coverage of wire bonds. The upper surface of substrate 15 of device 5 is thus composed of a flexible barrier material that provides a safe interface with the patient's environment in such a way that protects the electrical components but does not impede flexibility. Medical grade silicone can also be used to encapsulate the electronic components in order to further ensure biocompatibility, electrical compatibility as an encapsulating material for microelectronics, and for case of overall application.

In terms of power supply, device 5 provides for varying approaches to power source 50, which typically requires provision of a requisite voltage that is necessary to generate stimulating waveforms. Power source 50 may comprise single-use batteries, however discharge characteristics must be repeatable to ensure reliable delivery of pre-programmed stimulation patterns. A flat power discharge profile that will provide consistent power for longer periods (e.g., approximately 7 days or so) of stimulation is desirable, although the inventive electronics design also allows for a somewhat sloped discharge profile. Therefore, any battery chemistry can be used. The battery must be thin, small, durable and strong. Power supply 50 can be modified in 1.5-V increments as necessary, but generally will be either 1.5 V or 3.0 V. To this end, power source 50 is ideally thin and flexible as specifically described below in one illustrative embodiment, but it can nevertheless be of any suitable size and shape that can accommodate the aforementioned requirements. In one embodiment, the power source 50 is depicted as a single electrochemical cell. However, power source 50 need not be limited to one cell, but may include a plurality of connected electrochemical cells, galvanic cells, batteries, with/without electronics configured to regulate the electrical potential (voltage) to the level required by the particular body area of the subject. In some embodiments, the current and or voltage supplied by the power source is fixed and cannot be adjusted by a user, although stimulation controller 20 can provide for any direct stimulation capability. The thickness of the illustrative electrochemical cell or power supply 50 may be in the range of about 4-20 mm thick. By way of example, a suitable electrochemical cell may be a button or watch battery, such as a lithium coin battery providing approximately 40 mA-hr at 3V, may be utilized. However, this may in some cases prove too heavy and bulky, and as such, in alternative embodiments, power supply 50 may be provided in a 1.5-V cell with step-up circuitry, with total battery current consumption for a nominal stimulation pattern of ~1 mA, thereby giving a battery life of say, 240 hours with a 15% stimulation duty cycle, or may also be provided as a thin cell applied using a suitable printing technique. Recent developments in battery technology have led to the development of very low profile, flexible 'ribbon' batteries, such as PowerPaper™ batteries (available from Graphic Solutions. Inc., Chicago, Ill.), which are ultra-thin (<1 mm thick) flexible batteries that can be directly printed onto a variety of surfaces. The cathode and anode layers of these illustrative batteries are fabricated from proprietary ink-like materials, thereby creating a 1.5-V battery that is thin and flexible and does not require bulky casing or encapsulation. In addition, the materials used in this illustrative battery, zinc and manganese dioxide, are classified by the Federal Drug Administration (FDA) as environmentally friendly, non-hazardous and may be disposed of without restriction. These types of batteries are capable of providing up to 1 mA continuous current. However, these ribbon type batteries often do not provide adequate power for longer periods, and may be useful for more temporary applications. Terminals for connection thereto may be located in any desired location to connect to the specific cell employed and may acquire any suitable shape and size, depending on the specific application.

The invented device may be provisioned as a single-channel, single-pattern stimulator device, which would require a system control switch (not specifically depicted) to switch the operating state of device 5 between one of two states, off and on. However alternative embodiments of the device will also include the potential for multiple stimulation patterns and feedback to the clinician or technician through stimulation controller 20, which as discussed above, offers the capability for more sophisticated control, interrogation and feedback options. In providing such features, bi-directional wireless communication module 40 may further include an RF or an infrared communication link and protocol (such as an IrDA-based infrared communication link and protocol) that allows the ISSD to communicate via multiple channels with outside partner devices (not depicted) such as Personal Digital Assistants, computers, smart phones, tablets, lap tops, etc., so as to allow system control and retrieval of sensor data without a physical connection to device 5. In such an illustrative embodiment, the selected communication protocol might allow up to 256 units to be used in the same vicinity. If based on illustrative IrDA-type optical components, it is noted that the inherently narrow transmission focus thereof (approximately a 30 degree cone) can mitigate potential communications issues emanating from inventive device 5, because selection of a given partner device requires pointing the partner device at the inventive device 5 being programmed at any given time. Communication software can further be utilized for modifying stimulation parameters in stimulation controller 20 and for displaying stimulation waveform graphs on the partner device. To this end software to allow system control and retrieval of sensor data (e.g., outside control adjustment and feedback upload) using the link might be provided in accordance with the illustrative steps 610-670 as outlined in FIG. 6. Sensor data and other status parameters can be uploaded to the partner device and displayed to facilitate any necessary adjustments. Afterwards, any (bio) data provided from the sensors (electrodes 10) can be uploaded to the partner device for further analysis offline, if desired by a given medical professional. To this end, the aforementioned optional software package may also be provided with a graphical user interface (GUI) for use on a partner device connected to the inventive device, as employed by a medical professional.

When provided in accordance with the above, treatment device 5, including all device components, has an overall thin and flexible profile, which may suit the contour of a body area of a subject. Treatment device 5 may therefore be of any size, color and shape suitable for application to a desired body area. In some embodiments, the thickness of device 5 may limited to 10 mm to ensure flexibility, but may be thicker in other applications. The thickness of device 5 may also be dependent upon the type of material used and the flexibility of that material. In some embodiments device 5 may be partially and/or completely disposable. To this end, in some embodiments substrate layer 15 may be disposable, while the ISSD circuitry 60 may be reusable (modular, and therefore easily switched to a new replacement substrate layer 15), or alternatively, the whole device 5 may be deemed disposable. Regardless of which embodiment is chosen, device 5 must be stable over a wide range of temperatures and humidity levels, and may be used over all body areas of a patient or user, and to this end, may be designed or customized to fit any area of the body and to have any desirable size, according to the area to be treated. By way of further note, electrodes 10 can also be customized in terms of overall number, size, and distribution on substrate layer 15. The customization of electrodes is often less important when the application usage of device 5 is for pain treatments (which are better customized through the use of amplitude variations and the like for varied pain states). In the case of wound treatment, however, it is often important to be able to vary the aforementioned design parameters in order to adequately treat different types and sizes of wounds.

The device of the present invention can therefore be a fully integrated device or can be part of a kit with removable components so that the covering, battery source, etc. may be replaced as needed. The device may also be removed from the body area at the end of treatment time. Time of treatment can vary, and accordingly, the device in some embodiments can be removed from contact with the body area after a time period which can be predetermined, upon expiration of a timer, or which can be determined according to the desired treatment and/or until no more improvement can be seen. The treatment can optionally be a one-time treatment, or can be repeated in suitable time intervals any suitable number of times. Use of the present invention can facilitate temporary alleviation and elimination of the above conditions. Duration of effect can therefore be affected by time and frequency of application, stimulation pattern variables, type and amount of current used, and severity of condition. In one embodiment, the device is a dermal patch configured for home use. In other embodiments, the device can be applied in a supervised environment. To this point, treatment according to the present inventions may be beneficial in all body areas. Being thin, flexible and versatile in shape and form, the devices of the present invention can be designed to fit any area of the body and to have any desirable size, according to the area having the disorder.

One skilled in the art can appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

Novel Electrotherapy for Acute Infected Wounds as a Method for Inhibiting Planktonic and Bacterial Activity.

It is understood that wound infection delays healing and increases mortality. Increasingly, antibiotics are showing reduced efficacy in the face of multi-resistant bacteria. The increasing prevalence of multi-resistant bacteria indicates that novel approaches to infection control are needed as both alternative and adjunctive therapies to standard antibiotic regimes. Such infections are particularly challenging when biofilms are involved given that biofilms have protective coatings made up of polysaccharides and other components that shield the given bacteria colony in the biofilm from treatment. Hence, there is a clinical need for an intervention that can reduce incident infection, clear existing infection and accelerate healing, especially when a patient has an infection that exhibit biofilm colonies. The novel use of Electrical Stimulation (ES) as disclosed herein has the potential to address this clinical challenge by reducing incident infection, clearing existing infection and accelerating healing.

Both planktonic and biofilm bacterial wound infections can be positively impacted by the novel use of ES to improve healing rates in both acute and chronic wounds can be effectively treated. The novel system and methods relating to ES treatment as disclosed herein increases local metabolic activity of cells and tissue oxygenation (flesh healing), disrupts existing biofilm colonies, and even inhibits biofilm formation from the outset. Additionally, the novel system and methods relating to ES also reduces acute wound infection by bactericidal effects on many strains relevant for complications of acute traumatic wounds. These effects may be due to electrolysis products or to increases in bacterial membrane permeability. Sustained ES application in accordance with the present invention is bactericidal when applied to infected but unwounded skin, and additionally, increases blood flow and capillary density in compromised wounds, thereby speeding up healing rates thereof. The resulting efficacy of the present invention appears to vary with stimulation profile, which in at least one illustrative case, is that the primary ES factor being current density, thereby implying that the bactericidal effect is electrochemically mediated. Low-intensity electric fields (e.g., those having a field strength of 1.5 to 20 V/cm and current densities of 15 pA/cm2 to 2.1 mA/cm2) can combat the inherent resistance of biofilm bacteria to biocides and antibiotics. Biofilm infections are a well known for being difficult to eradicate, especially when compared with planktonic cell of the same species of bacteria. The novel application of electrochemically mediated treatment with the inventive device offers a bioelectric effect that reduces the concentrations of the antibacterial agents needed to kill biofilm bacteria when compared with those needed to kill planktonic cells of the same species. The electric field from the novel ES device and method can aid the disruption or penetration of the antibacterial agents through the protective polysaccharide and other coatings that shield the biofilm. This penetration is, in one illustration, accomplished by a form of electrophoresis that may augment the electrochemical generation of resulting surface agents that enhance the efficacy of given antibacterial.

In accomplishing the above, the present invention therefore provides for a method for using an ISSD for wound therapy as well as for infection control, including for difficult infections like biofilm based infections. To this end, in one illustrative embodiment, the method might comprising the following steps of: (i) assessing a wound and/or infection state; (ii) applying a customized ISSD patch with electrodes 10 and a flexible substrate 15 immediate to a wound location; (iii) attaching an encapsulated power/control module 20 to said customized ISSD patch with electrodes and the flexible substrate 15; (iv) setting ISSD controls, including setting at least one of the following of a power profile or at least one customized stimulation pattern; (v) initiating ES power and sequences on a resulting set up; and (vi) monitoring wound and at least one of the following of battery power, impedance, and temperature. Additionally, the inventive method may further comprise: (vii) formulating a customized electrode 10 pattern according to the step of assessing a wound type and infection state; (viii) fabricating said customized electrode 10 pattern by various techniques, including foil, additive or 3-D printing techniques, or alternatively, by traditional deposition techniques; and (ix) combining said customized electrode 10 pattern with selected flexible substrate 15 as a resulting patch 5' for patient wound therapy. Also the method may additionally include: (x) attaching an encapsulated power/control module 20 to customized ISSD patch 5' with electrodes 10 and a flexible substrate 15, and additionally; (xi) combining a customized disposable flexible substrate 15 with a re-usable, sterilizable encapsulated power/control module 20. What is specifically meant by encapsulated power module 20 being sterilizable or having a sterilizable encapsulation is that it is encapsulated in a plastic or other type of complete encapsulation that can seal off the electronics therein from the harmful effects of water or chemicals that may be used in the course of sterilization at a level that can kill microorganisms. Separately, it is noted that optional provision is contemplated for attaching a power source 50 comprising a rechargeable battery (power supply 50) with capacity of at least 450 mA-h.

In applying the above inventive method in a clinical setting, one illustrative approach calls for the novel approach of providing treatment and monitoring of wounds and infections concurrently or at same time. Thus, one employing this novel approach might be able to simultaneously or concurrently treat and monitor wounds and infections through the following steps of: (i) applying a customized ISSD patch 5' with electrodes 10 and a flexible substrate 15 immediate to a wound of a patient; (ii) electrically connecting an encapsulated power and control module 20 to customized ISSD patch 5'; (iii) establishing a wireless communication connection for remote control between a control module 40 and encapsulated power and control module 20; (iv) monitoring ongoing wound and infection indicia over a course of time; (v) establishing, based upon the preceding step of monitoring ongoing wound and infection indicia over a course of time, a dynamic (e.g., potentially revisable depending on changes to identified wound and infection indicia) wound treatment ES profile for execution over said course of time; (vi) establishing, monitoring ongoing wound and infection indicia over a course of time, a dynamic infection control ES profile for execution over the course of time; and (vii) executing, over the course of time, said dynamic wound treatment ES profile and the dynamic infection control ES profile at the control module. Additionally, the method may further include processing steps (iv)-(vi) through an open loop program option or a closed loop option. An open loop program option may be further described in one embodiment as: In the open-loop embodiment the medical professional will receive a report of the wound/infection status transmitted from the ISSD. The medical professional will be able to alter the ES profile remotely to maintain optimal treatment. In the closed-loop embodiment, the medical professional will receive a report of the wound/infection status transmitted from the ISSD and the ISSD will adjust the ES profile in real time based on the wound indicia being monitored.

In the above, it is noted that the wound and infection indicia may include particulars such as wound temperature, wound impedance, and wound pH. Monitoring such particulars is advantageous inasmuch as it has now been found that impedance decreases over time where a wound is healing and/or where infection presence is decreasing, and similarly, temperature exhibits similar paradigms of decrease. Additionally, the step of monitoring while treating is further advantageous in that all wound healing (and infection resolution) goes through different stages over time, and consequently, it has now been found that the inventive approach of utilizing treatment factors such as pulse width, pulse interval, and interpulse amplitude variables is to be pursued in a dynamic fashion, whereby the same are increased or decreased over time increments and over the overall course of time in response to the respective stage of healing or infection resolution. Similarly, the monitored presence of say, just an infection without wound presence normally entails utilization of different treatment factors, such as a relatively lower current than that which is normally employed compared to wound healing. Also similarly, monitoring for biofilms as opposed to planktonic infections may alter the treatment factors, just as monitoring for an acute infection turning into a chronic infection, because a chronic infection (unlike acute) may normally imply wound treatment factors in addition to purely infection treatment factors. Hence, the infection state as monitored can drive the electrical pattern and any accompanying customization therewith.

It is further noted that the aforementioned method for simultaneous treatment and monitoring of wounds and infections may provide that the step of monitoring ongoing wound and infection indicia over a course of time, as well as the step of executing the dynamic wound treatment ES profile and the dynamic infection control ES profile may both be effectuated remotely through use of wireless communication, such as bi-directional wireless module(s) 40 as depicted in FIG. 1. In some cases, control module 20 has wireless communication module 40 encapsulated therewith.

Illustratively, the following particulars were observed in one exemplary usage of the inventive system and apparatus for treating wound infections:

Example 1—Electrical Stimulation (ES) Promotes the Healing of Ischemic Wounds

Approach:

The effects of varying clinically relevant ES variables were evaluated using a modified version of the Gould F344 rat ischemic wound model. Stimulation was delivered using the novel lightweight integrated, single-channel, current-controlled ISSD as further disclosed herein. Customized ES patterns in accordance with the novel approach disclosed herein were utilized, which, in this illustration, included stepwise variation, indicating the effects of five (5) different stimulation paradigms within an appropriate current density range to be studied. These five (5) different illustrative stimulation paradigms included: Pattern 1: pulse amplitude 4 mA, pulse width 100 µs, interpulse interval 50 ms; Pattern 2: pulse amplitude 2 mA, pulse width 100 µs, interpulse interval 50 ms; Pattern 3: pulse amplitude 6 mA, pulse width 100 µs, interpulse interval 50 ms; Pattern 4: pulse amplitude 4 mA, pulse width 150 µs, interpulse interval 50 ms; and Pattern 5: pulse amplitude 4 mA, pulse width 100 µs, interpulse interval 40 ms. Within each of the aforementioned five (5) respective groups, 8-10 animals were treated for 28 days or until the ischemic wounds were healed, and additionally, 5 animals were treated for just 12 days. Eight (8) rats received sham devices as a control. A quantitative multivariable outcomes assessment procedure was used to evaluate the effects of ES.

Results:

Ischemic wounds treated with a decreased interpulse interval (IPI) had the highest rate of complete wound closure at three (3) weeks. Wounds treated with decreased pulse amplitude (PA) had a lower proportion of closed wounds than sham (control) ischemic wounds and showed sustained inflammation with a lack of wound contraction.

Results According to Specific Illustrations of Exemplary Stimulation Variable Settings:

Acute Infected Wounds:

ES was delivered by the ISSD with a 10% duty cycle for up to 28 days or until all treatment wounds appeared to be fully healed. The median values selected for proof-of concept testing were pulse amplitude 11 mA, pulse width 110 µs, pulse frequency 17 Hz. By 21 days post-injury, ES treated infected wounds were 84% smaller than untreated control wounds.

Chronic Wounds:

Optimal stimulator parameters will vary depending on wound type and extent, but benefits have been seen for a wide range of parameters. The optimal treatment parameters for delivery of effective ES for chronic wound therapy are therefore guided by the underlying physiological effects. In pre-clinical testing, ES delivered by the ISSD with a 10% duty cycle with pulse amplitude 4 mA, pulse width 100 µs, interpulse interval 40 ms had the highest rate of complete wound closure at 3 weeks.

CONCLUSION

The systematic study of innovatively varying ES paradigms using the novel ISSD provides insight into the advantageous use of ES in ischemic wound healing. This conclusion is based upon the following findings. Specifically, clinically appropriate ES can more than double the proportion of ischemic wounds closed by three (3) weeks in this model. Ninety percent (90%) of wounds treated with a decreased IPI healed by twenty-one (21) days compared with only twenty-nine percent (29%) of ischemic wounds treated with decreased PA, which appears to inhibit healing.

It is further noted that, in the above example (as well as for other illustrations of the novel method) the innovative ISSD undergirded much of the advantageous results. Specifically, the innovative delivery of power has superior reliability, and is able to deliver ES over an extended period of time that heretofore has not been realized. Thus, the innovations of: customized electrodes, customized pulse, customized width, intermittent v. continuous pulsing, etc as disclosed herein are indeed novel, and furthermore, the actual use of ES in both acute and chronic wounds (especially in combating troublesome biofilms) is heretofore unknown.

The above approach can be employed in human (in vivo) applications in order to speed up healing of both chronic and acute wounds, as well as for reducing infections of both planktonic and biofilm types, especially in topical rather than systemic applications. In doing so, one illustrative method might include some or all of the following exemplary steps: 1) Assess wound type and/or infection type; 2) Formulate customized electrode pattern by considering, for example wound size; 3) Fabricate customized electrode pattern by various techniques, including additive or 3-D printing techniques, or alternatively, by traditional deposition techniques, combine with selected flexible substrate as resulting patch for patient wound; 4) Apply patch immediate to wound location, attach ISSD controls; 5) Set power profile or customized profile in accordance with particulars described elsewhere herein; 6) Initiate ES power and sequences on resulting set up; 7) Monitor battery power, impedance, and temperature. Thereafter, if the measure impedance increases over time from a base impedance as measured, then that means that the target wound is healing. Also, operators should monitor the measured temperature at the wound site, as this factor is typically related to infection level, such that elevated temperature indicates infection activity overall, although it is to be noted that this normally is more indicative of planktonic infections which are often more biologically active, rather than biofilm based infections which tend to be more stable; 8) Retain patch with ES treatment on for a specified period of time. In one exemplary usage where the system is complimentary to antibiotic use, one illustrative period of use is for approximately seven (7) days. Note that this treatment period may vary, in accordance with wound type, patient history, electrode customization and ES pattern profiles and current density chosen by the medical provider.

Of additional note, is the understanding that in some embodiments, one may dispense with steps 2 and 3 in cases where the customized electrode pattern has already been fabricated off site and combined with the flexible substrate for use as part of a readily accessible stockpile or pre-configured customized patches that are suitable for a specific wound types. Such provision would eliminate the need to have fabrication equipment on site. In such cases, the stock customized patches could be respectively produced in mass according to shape and size (depending on the areas of body being treated) and for type of wound (e.g., a more electrodes or a higher density of electrodes in a given electrode pattern might be used for wounds such as chronic wounds, or for acute traumatic or surgical wounds, and the like).

It is noted that the aforementioned can be applied to more than just the actual flesh of human patients undergoing the innovative ES treatment with the novel apparatus. Specifically, the novel method and apparatus can also be adapted in an alternate embodiment, to medical device surface treatments, such as for oral biofilms, mouth guards, orthodontics, tracheostomy tubes, endotracheal tubes, indwelling catheters as well as other classes of catheter, and in general other medical devices that are susceptible to infections, especially those caused by biofilm buildup. In adapting to the same, an exemplary approach might be as follows: to provide a tracheostomy tube with integrated conductive regions which can be used to deliver bactericidal stimulation, a flexible lining for a mouth guard bath with integrated electrodes that can be activated to deliver bactericidal stimulation while the fixture is being cleaned.

What is claimed is:

1. A method comprising:
applying a flexible and customized Integrated Surface Stimulation Device (ISSD) patch over or proximate to a wound, wherein the ISSD patch comprises electrodes and at least one temperature sensor, wherein an encapsulated power and control module is electrically connected to the electrodes and at least one temperature sensor of the ISSD patch, wherein the encapsulated power and control module is configured to measure, between at least two electrodes of the electrodes of the ISSD patch, at least one wound impedance associated with the wound location, wherein the at least one temperature sensor is configured to measure at least one wound temperature associated with the wound, wherein applying the ISSD patch over or proximate to the wound comprises positioning each of the electrodes of the ISSD patch at margins of the wound;
establishing remote communication between a remote control module and the encapsulated power and control module;
using the encapsulated power and control module to control delivery of electrical stimulation to the wound location by the electrodes of the ISSD patch by providing current that travels directly between a first electrode and a second electrode of the electrodes of the ISSD patch, wherein the first electrode is at a first position at the margins of the wound, and wherein the second electrode is at a second position at the margins of the wound;
receiving, through the remote control module, a first output indicative of the at least one wound impedance or the at least one wound temperature;
determining, by the remote control module, an infection status of the wound and a healing status of the wound based at least in part upon the first output;
determining and executing, by the remote control module, a variable Electrical Stimulation (ES) profile through communication with the encapsulated power and control module, wherein the electrodes of the ISSD patch deliver electrical stimulation in accordance with the ES profile, wherein the ES profile is selected to promote wound healing; and adjusting, by the remote control module, the ES profile in real time based upon at least the first output received from the encapsulated power and control module.

2. The method of claim 1, wherein the remote control module determines the infection status of the wound based upon the at least one wound temperature.

3. The method of claim 2, wherein the remote control module determines changes in wound temperature, and wherein the changes in wound temperature are indicative of the healing status of the wound.

4. The method of claim 2, wherein the remote control module determines an increase in wound temperature, wherein the increase in wound temperature is indicative of infection of the wound.

5. The method of claim 1, wherein the first output is indicative of the at least one wound impedance, and wherein the method further comprises:

receiving, through the remote control module, a second output indicative of the at least one wound temperature, wherein the remote control module determines the infection status of the wound and the healing status of the wound based at least in part upon the first and second outputs.

6. The method of claim 5, wherein the encapsulated power and control module comprises a battery, wherein the method further comprises:

receiving, through the remote control module, a third output indicative of battery power, wherein, based upon the third output, the remote control module determines a remaining time before battery recharge is required.

7. The method of claim 1, wherein the electrodes of the ISSD patch are electrically connected with the encapsulated power and control module by electrical interconnects that are fabricated on the ISSD patch.

8. The method of claim 7, wherein the encapsulated power and control module comprises electrical interconnects fabricated on the encapsulated power and control module, and wherein the electrical interconnects of the encapsulated power and control module mate with the electrical interconnects fabricated on the ISSD patch.

9. The method of claim 1, wherein the ES profile comprises an interpulse interval that is less than 50 milliseconds.

10. The method of claim 9, wherein the wound is an ischemic wound.

11. The method of claim 1, wherein the ES profile comprises an amplitude that is greater than 2 milliamps.

12. The method of claim 11, wherein the wound is an ischemic wound.

13. The method of claim 1, wherein the remote control module determines the healing status of the wound based upon the at least one wound impedance, and wherein an increase in impedance associated with the wound is indicative of progressive healing of the wound.

14. The method of claim 1, wherein the encapsulated power and control module comprises first and second circuits that respectively determine the infection status and the healing status of the wound.

15. The method of claim 1, wherein the remote control module comprises software that, when executed, determines the infection status and the healing status of the wound.

16. The method of claim 1, wherein the encapsulated power and control module is completely encapsulated, and wherein the complete encapsulation seals off electronics of the power and control module.

17. The method of claim 1, wherein the ISSD patch comprises a disposable substrate.

18. The method of claim 1, further comprising:

determining, by the remote control module, ischemia of the wound based on the at least one wound temperature; and adjusting the variable ES profile upon detection of ischemia of the wound.

19. A method for simultaneous treatment and monitoring of wounds and infections, the method comprising:

applying an Integrated Surface Stimulation Device (ISSD) patch to a wound, wherein an encapsulated power module is electrically connected to electrodes of the ISSD patch, wherein applying the ISSD patch to the wound comprises positioning each of the electrodes of the ISSD patch at margins of the wound;

establishing a wireless communication connection for remote control between a control module and the encapsulated power module;

wirelessly monitoring, in real-time, by the control module and the encapsulated power module, wound and infection indicia over a period of time, wherein the wound and infection indicia comprises at least one of wound temperature, wound impedance, or wound pH;

establishing, by the control module, and based upon the real time monitoring of wound and infection indicia over the period of time, a dynamic wound treatment electrical stimulation (ES) profile for execution over the period of time; and executing, over the period of time, by the control module and the encapsulated power module, the dynamic wound treatment ES profile to cause electrical stimulation to the wound location by the electrodes of the ISSD patch by providing current that travels directly between a first electrode and a second electrode of the electrodes of the ISSD patch, wherein the first electrode is at a first position at the margins of the wound, and wherein the second electrode is at a second position at the margins of the wound, wherein the control module adjusts the ES profile in real time based upon at least the first output received from the encapsulated power module.

20. The method of claim 19, wherein at least one of a pulse width, a pulse interval, or an interpulse amplitude of the dynamic wound treatment ES profile is increased or decreased by the control module in response to the real time monitoring of the wound and infection indicia.

* * * * *